United States Patent [19]

Becker et al.

[11] Patent Number: 4,898,993
[45] Date of Patent: Feb. 6, 1990

[54] PROCESS FOR PREPARING 2-TERT-BUTYL-4-METHOXYPHENOL

[75] Inventors: Abram Becker, Paris, France; Nurit Kornberg; Berta Croitoru, both of Beer-Sheva, Israel

[73] Assignee: Bromine Compounds Limited, Israel

[21] Appl. No.: 143,403

[22] Filed: Jan. 13, 1988

[30] Foreign Application Priority Data

Jan. 21, 1987 [IL] Israel ........................................ 81339

[51] Int. Cl.$^4$ ............................................. C07C 41/06
[52] U.S. Cl. ..................................................... 568/658
[58] Field of Search .......................................... 568/658

[56] References Cited

U.S. PATENT DOCUMENTS 2,835,650 5/1958 Nelson et al. ...................... 568/658
4,218,567 8/1980 Manchand et al. ................. 562/475

Primary Examiner—Bruce Gray
Attorney, Agent, or Firm—Lerner, David, Littenberg, Krumholz & Mentlik

[57] ABSTRACT

A process is described which permits to prepare substantially pure 2-tert-butyl-4-methoxyphenol, by reacting 4-bromo-2-tert-butylphenol with a methoxide in an organic solvent.

The process permits to obtain a substantially pure 2-isomer, and avoids the need for the separation of the 2- and 3-isomers.

10 Claims, No Drawings

PROCESS FOR PREPARING 2-TERT-BUTYL-4-METHOXYPHENOL

BACKGROUND OF THE INVENTION

The present invention relates to a process for the preparation of 2-tert-butyl-4-methoxyphenol.

2-Tert-butyl-4-methoxyphenol, hereinafter referred to as BHA (butylated hydroxyanisole) for the sake of brevity, is a well known preservative for food products. The process commonly employed for its preparation involves methylating hydroquinone to obtain 4-methoxyphenol which is then reacted with isobutylene to yield BHA. This process, however, presents several disadvantages. In the first reaction, dimethylation of hydroquinone also takes place, leading to an undesired by-product. The second reaction, viz., the butylation of 4-methoxyphenol, is not selective, leading to a mixture of 2- and 3-tert-butyl-4-methoxyphenol isomers, typically a mixture of 70% 2-isomer and 30% 3-isomer.

The separation of the 2- and 3-BHA isomers is expensive and very difficult, since the purification of the 2-isomer is carried out by multiple crystallization. Furthermore, BHA must contain at least 85% of the 2-isomer; commercially available products are sold with a 90–93% content of the 2-isomer. It is therefore clearly desirable to provide a process by which the useful 2-BHA isomer can be recovered in high yield and with high purity.

It is an object of the present invention to provide a simple and economic process by which substantially pure 2-BHA isomer can be prepared.

DETAILED DESCRIPTION OF THE INVENTION

The process for the preparation of 2-tert-butyl-4-methoxyphenol is characterized in that 4-bromo-2-tert-butylphenol is reacted with a methoxide in an organic solvent, in the presence of a catalyst and of a formamide.

According to a preferred embodiment of the invention the formamide is N,N-dimethylformamide. According to another preferred embodiment of the invention the formamide is 4-formylmorpholine.

The content of the formamide in the reaction mixture may vary between 1.5% to 40% by volume of the 4-bromo-2-tert-butylphenol, and is preferably between 10% and 20%. As it will be apparent to a person skilled in the art, this content of the formamide is very low, as compared with previously disclosed processes employing, e.g., dimethylformamide, which require several volumes of DMF per volume of reactants. For example, U.S. Pat. No. 4,218,567 relates to the methoxylation of brominated aromatic compounds in the presence of copper salts and DMF, with $CH_3ONa$. The quantities of DMF employed are very high, for instance, 312 ml DMF for 165 g of 3,5-dibromo-4-hydroxybenzaldehyde (Example 2), and 450 ml DMF for 214.4 g of 3-methoxy-4-hydroxy-5-bromobenzaldehyde (Example 4). The low amount of formamide required in the process of the invention is another considerable advantage of the invention.

According to a preferred embodiment of the invention, the catalyst is selected from among:

(a) a catalytic system comprising a mixture of copper, cuprous bromide, bronze and potassium iodide; and (b) a catalytic system comprising a mixture of copper hydroxycarbonate and sodium sulphite.

The most preferred catalyst is the catalytic system (a). When employing the abovementioned catalyst (a) it advantageously comprises, as a percentage based on the weight of 4-bromo-2-tert-butylphenol:

(1) about 0.5% to 1% Cu, preferably about 0.5%;
(2) about 0.9% to 3.6% CuBr, preferably about 1.8%;
(3) about 0.25% to 1% bronze, preferably about 0.6%; and
(4) about 0.25% to 1% KI, preferably about 0.6%.

When it is desired to operate with the abovementioned catalyst (b), a preferred composition comprises, as a percentage based on the weight of 4-bromo-2-tert-butylphenol:

(1) about 1.0% to 5% $CuCO_3Cu(OH)_2$, preferably about 2% to 3%; and
(2) about 2% to 10% sodium sulphite, preferably about 4% to 6%.

According to a preferred embodiment of the invention, the methoxide is sodium methoxide and the solvent is methanol. The methanol employed should be substantially free from water, and preferably should contain less than 0.1% of water. Other methoxides, such as potassium methoxide, can be employed in the process of the invention, but sodium methoxide is preferred for practical reasons.

The reaction is preferably carried out at a temperature between about 70° C. and the reflux temperature of the reaction mixture (about 100°–110° C.). When employing methanol as the solvent, the preferred reaction temperature is in the range of about 90° to 95° C.

As stated, the process of the invention yields substantially pure (>99%) 2-tert-butyl-4-methoxyphenol. Even before workup, purities as high as 98–99% of BHA are obtained. This highly pure BHA product also forms a part of the present invention.

When operating according to the process of the invention, with the preferred catalyst (a), yields of 90% or higher can be obtained in one reaction step. Furthermore, when operating with the catalyst (a) the resulting BHA is uncontaminated by residual bromine. No traces of bromine are found in the BHA so obtained, when tested by X-ray and by GCMS. This is, of course, an advantage of the said preferred catalyst.

The above and other characteristics and advantages of the invention will be better understood through the following illustrative and non-limitative examples.

EXAMPLE 1

To a four-necked 3 liter flask, containing 1350 g of a 30% solution of $CH_3ONa$ in $CH_3OH$ ($CH_3ONa$ content: 7.5 moles), there were added 696 g of 4-bromo-2-tert-butylphenol (3.04 mole), 25.5 g of anhydrous $CuCO_3.Cu(OH)_2.0.5H_2O$, 24.5 g of anhydrous $Na_2SO_3$ and 10 ml of dimethylformamide. The mixture was heated under a nitrogen atmosphere, methanol was distilled off during 4.5 hours at a flask temperature of 85°–95° C., and 1050 ml of methanol were collected. To the mixture remaining in the flask there were added 400 ml of distilled water. The exothermic reaction raised the temperature to 75° C. Further distillation of the water-methanol mixture provided additional 350 ml of wet methanol. The reaction medium was neutralized with 470 ml of a 48% HBr solution to pH 7 at a temperature of 70°–75° C. At the end of the neutralization stage, 100 ml of toluene were added, the mixture was cooled to 55° C. and the copper was filtered off. The filter cake was washed with alternate portions of toluene and water, to a total of 100 ml of water and 150 ml of toluene. After filtration and washing, the organic and aqueous layers were separated and the aqueous layer was extracted with three 100 ml portions of toluene. All toluene extracts were then combined and the toluene was evaporated on a rotary evaporator. The crude product, 561 g, was treated with 90 ml of a 50% aqueous solution of hydrazine for 30 minutes at 70° C. The hydrazine solution was afterwards distilled off at 120°/25 mmHg. Distillation was continued at reduced pressure (1–2 mmHg) at a flask temperature of 110°–180° C. and head temperature of 98°–135° C. 456 g of 99.4% pure BHA were obtained in 85% yield.

G.C. analyses were carried out with a glass column 1% SP 1240DA. 3 ft 2 mm. Temp(1)=100°; Temp(2)=150°; Hold(1)=0; Hold(2)=8; Inj.=230°; Det.=230°; Rate=10°/min. Retention times (min.): Phenol, 1.8; 2-tert-butylphenol, 2.9; 4-methoxyphenol, 3.9; BHA, 5.8 and 4-bromo-2-tert-butylphenol, 6.8.

G.C. results after 4.5 hours of reaction, before workup: 99.1% BHA; 0.2% phenol; 0.6% 2-tert-butylphenol; 0.1% 4-methoxyphenol.

EXAMPLE 2

To a four-necked 1 liter flask, containing 540 g of a 30% solution of $CH_3ONa$ in $CH_3OH$ (3 moles $CH_3ONa$) there were added 232 g of 4-bromo-2-tert-butylphenol (1.0 mole), 1.2 g copper powder, 4.2 g cuprous bromide, 1.4 g bronze powder (pre-activated in a solution of 1% iodine in acetone and washed with diluted hydrochloric acid, according to A. I. Vogel, "Practical Organic Chemistry", 4th Ed., p.285), 1.4 g KI and 40 ml of dimethylformamide. The mixture was heated under a nitrogen atmosphere and methanol was distilled off during 4 hours at a flask temperature of 85°–96° C.; 375 ml of methanol were collected. To the mixture remaining in the flask there were added 140 ml of distilled water. The exothermic reaction raised the temperature to 75° C. Further distillation of the water-methanol mixture provided additional 200 ml of distillate. The reaction medium was neutralized with 170 ml of a 48% HBr solution to pH 7 at a temperature of 70°–75° C. Following neutralization, 50 ml of toluene were added, the mixture was cooled to 55° C. and the copper was filtered off. The filter cake was washed with alternate portions of toluene and water, to a total of 40 ml of water and 120 ml of toluene. At the end of the filtration and washing steps, the organic and aqueous layers were separated and the aqueous layer was extracted with three 40 ml portions of toluene. All toluene extracts were then combined and the toluene was distilled off on a rotary evaporator. The crude product, 187.3 g, was distilled at reduced pressure (1–2 mmHg) at a flask temperature of 96°–180° C. and head temperature of 92°–120° C.; 167.5 g of 99.3% pure BHA were obtained in 92.4% yield.

G.C. results at the end of reaction and before workup: 98.9% BHA; 0.2% 2-tert-butylphenol; 0.8% 4-methoxyphenol.

EXAMPLE 3

Operating as in Example 2, but using 540 g of a 30% solution of $CH_3ONa$ in $CH_3OH$, 232 g of 4-bromo-2-tert-butylphenol, 6.12 g of $CuCO_3.Cu(OH)_2.0.5H_2O$ and 40 ml dimethylformamide, 164.8 g of 97.2% pure BHA were obtained, in 89% yield.

G.C. results after completion of the reaction, before workup: 98.8% BHA; 0.3% phenol; 0.5% 2-tert-butylphenol; 0.1% 4-methoxyphenol.

EXAMPLE 4

Operating as in Example 2, but using 540 g of a 30% solution of $CH_3ONa$ in $CH_3OH$, 232 g of 4-bromo-2-tert-butylphenol, 10.7 g $Cu(OOCCH_3)_2.H_2O$ and 40 ml dimethylformamide, 160 g of 96.8% pure BHA were obtained in 86% yield.

G.C. results after completion of the reaction, before workup: 98.3% BHA; 0.3% phenol; 0.55% 2tert-butylphenol; 0.5% 4-methoxyphenol.

EXAMPLE 5

Operating as in Example 1, but employing 5.7 g of 4-bromo-tert-butylphenol, 12 g of a 30% solution of $CH_3ONa$ in $CH_3OH$, 0.06 g Cu, 0.21 g of CuBr and 3 ml of 4-formylmorpholine instead of dimethylformamide, the reaction was completed in 6 hours at a reaction temperature of 85°–90° C. G.C. results after completion of the reaction, before workup: 96.2% BHA; 0.6% phenol; 1.1% 4-bromo-2-tert-butylphenol; 1.1% 4-methoxyphenol.

EXAMPLE 6

Operating as in Example 2, but using 540 g of a 30% solution of $CH_3ONa$ in $CH_3OH$, 232 g of 4-bromo-2-tert-butylphenol, 6.12 g of $CuCO_3.Cu(OH)_2.0.5H_2O$, 13 g $Na_2SO_3$ and 40 ml dimethylformamide, 162.4 g of 98% pure BHA were obtained in 85% yield.

GC results after completion of the reaction, before workup: 98.8% BHA, 0.3% phenol, 0.5% 2-tert-butylphenol, 0.2% 4-methoxyphenol.

The above description and examples have been provided for the purpose of illustration and are not intended to be limitative. Many variations can be effected in the process of the invention. For instance, different catalysts or catalytic systems can be used and lower reaction temperatures can be employed or different and comparable reagents or proportions thereof can be used, all without exceeding the scope of the invention.

We claim:

1. A process for the preparation of 2-tert-butyl-4-methoxyphenol comprising reacting 4-bromo-2-tert-butylphenol with a methoxide in an organic solvent, in the presence of a formamide and a catalyst selected from the group consisting of:
   (a) a catalytic system comprising a mixture of from about 0.5% to about 1% copper, from about 0.9% to about 3.6% cuprous bromide, from about 0.25% to about 1% bronze, from about 0.25% to about 1% potassium iodide, based upon the weight of said 4-bromo-2-tert-butylphenol; and
   (b) a catalytic system comprising a mixture of from about 1.0% to about 5% copper hydroxycarbonate, and from about 2% to about 10% sodium sulphite based upon the weight of said 4-bromo-2-tert-butylphenol.

2. The process of claim 1, wherein the formamide is N N-dimethylformamide.

3. The process of claim 1, wherein the formamide is 4-formylmorpholine.

4. The process of claim 1, wherein the formamide is present in an amount between about 1.5% to about 40% by volume of the 4-bromo-2-tert-butylphenol.

5. The process of claim 1, wherein the methoxide is sodium methoxide.

6. The process of claim 1, wherein the solvent is methanol.

7. The process of claim 1, wherein the reaction is carried out at a temperature between about 70° C. and the reflux temperature of the reaction mixture.

8. The process of claim 1, wherein said catalytic system (a) comprises a mixture of about 0.5% copper, about 1.8% cuprous bromide, about 0.6% bronze and about 0.6% potassium iodide, based on the weight of said 4-bromo-2-tert-butylphenol.

9. The process of claim 1, wherein said catalytic system (b) comprises a mixture of from about 2% to about 3% copper hydroxycarbonate and from about 4% to about 6% sodium sulphite, based on the weight said 4-bromo-2-tert-butylphenol.

10. The process of claim 4, wherein said formamide is present in amount between about 10% and about 20% by volume of said 4-bromo-2-tert-butylphenol.

* * * * *